United States Patent [19]  
Bayha et al.

[11] Patent Number: 4,636,293  
[45] Date of Patent: Jan. 13, 1987

[54] INTERNALLY HEATED OXYGEN SENSOR, PARTICULARLY FOR USE WITH INTERNAL COMBUSTION ENGINES

[75] Inventors: Kurt Bayha, Oberriexingen; Helmut Weyl, Schwieberdingen, both of Fed. Rep. of Germany

[73] Assignee: Robert Bosch GmbH, Stuttgart, Fed. Rep. of Germany

[21] Appl. No.: 715,656

[22] Filed: Mar. 25, 1985

[30] Foreign Application Priority Data

Jun. 27, 1984 [DE] Fed. Rep. of Germany ....... 3423590

[51] Int. Cl.$^4$ ............................................ G01N 27/58
[52] U.S. Cl. .................................... 204/428; 204/427
[58] Field of Search ................ 204/428, 427; 219/345, 219/544; 174/88 R; 338/34

[56] References Cited

U.S. PATENT DOCUMENTS

| 3,694,627 | 9/1972 | Blatchford | 219/345 |
| 4,127,464 | 11/1978 | Ichikawa | 204/428 |
| 4,219,399 | 8/1980 | Gruner | 204/428 |
| 4,357,526 | 11/1982 | Yamamoto | 219/544 |
| 4,556,475 | 12/1985 | Bayha | 174/88 |

Primary Examiner—Arthur T. Grimley  
Assistant Examiner—Jane K. Lau  
Attorney, Agent, or Firm—Frishauf, Holtz, Goodman & Woodward

[57] ABSTRACT

To provide an easily manufactured and easily connected heater element for a tubular ion-conductive body (26) forming a sensing element (24) of the oxygen sensor, the heater element (35) comprises a plate-like substrate (36) of insulating material, e.g. ceramic, which, at its inner end is wider than at the end fitting into the inside of the tubular ion-conductive body, the conductors leading to the heater being formed as conductive tracks spaced apart from each other by a greater distance at the inner end, adjacent connection zones (37/3), than close to the heater zone (37/1), the plate-like substrate, at the inner portion, being essentially trapezoidal and terminating in an end edge (36') which forms the wider side of the trapezoid. Electrical connection to the connection zones (37/3) and simultaneous retention of the plate-like body (36) within the sensor, are obtained by engaging the connection zones with bent-over hook-like spring wires (58, 59) pressing the plate-like body in the region of the connection zones against an abutment surface (55) formed within an insulator (40) located in the sensor.

7 Claims, 3 Drawing Figures

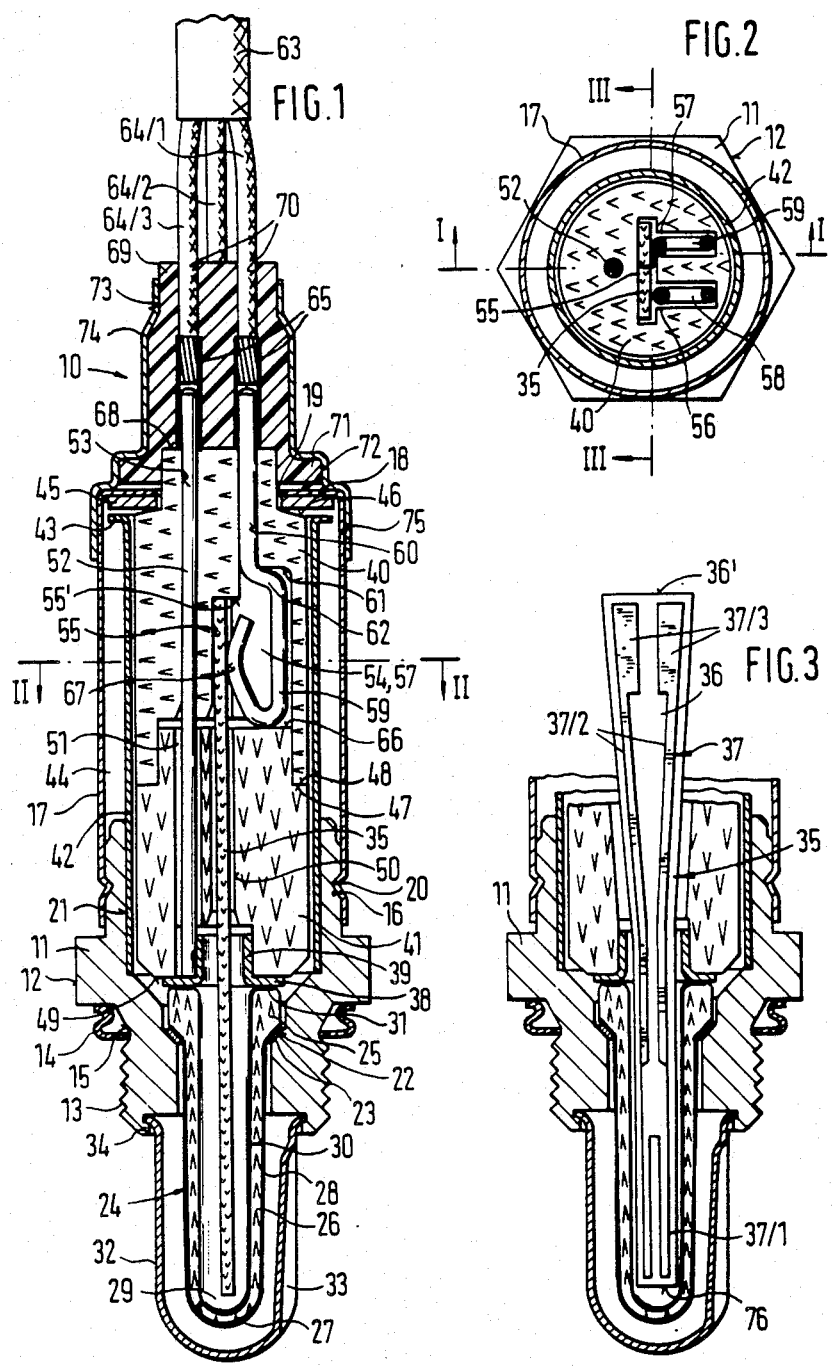

INTERNALLY HEATED OXYGEN SENSOR, PARTICULARLY FOR USE WITH INTERNAL COMBUSTION ENGINES

Reference to related patents and utility model:
U.S. Pat. No. 3,694,627, BLATCHFORD et al, assigned to Whirlpool Corp.
U.S. Pat. No. 4,556,475, by the inventors of the present application, BAYHA and WEYL.
German Utility Model DE-Gbms 81 01 584.

The present invention relates to an oxygen sensor, and more particularly to a sensor to determine the oxygen content in exhaust gases resulting from a combustion process, for example exhaust gases from an internal combustion engine.

1. Background.

Various types of oxygen sensors are known, see, particularly, the prior patent by the inventors hereof, U.S. Pat, No. 4,556,475, July 6, 1984. The sensor described in the earlier application utilizes a solid electrolyte tube, closed off at the bottom at the side facing the test or sensing gas. A heating element, in rod form, extends within the hollow solid electrolyte tube. The rod-like heating element is formed, at its end portions remote from the sensing end, with surface regions defining electrical terminal connections, against which compression contact terminals, in wire form, are engaged. The compression contacts are connected to electrical conductors which, in turn, are carried towards the outer region of the sensor at a terminal end portion thereof.

The system works well; it has been found, however, that the rod heating elements used in connection with the heaters are expensive to manufacture in mass production, since the requirement for materials is comparatively high, and printing of metallic conductive tracks on the round surfaces of the rod-like substrate is complicated. Various types of conductive tracks can be applied to various substrates, used as electrical heating elements—see, for example, the referenced U.S. Pat. No. 3,694,627.

2. The Invention.

It is an object to improve an oxygen sensor having a closed tube into which a heater extends, by providing a heating element which can be easily made, requires less material, and hence, overall, reduces the cost of such a sensor.

Briefly, the heater element is formed as conductive tracks on a plate-like substrate of insulating material, for example aluminum oxide, having a dimension at the inner end which is wider than the dimension of the end projecting into the interior of the hollow electrolyte sensor tubes. Heating conductors, for example as conductive tracks, are located on the substrate. Spaced electrical connection tracks are likewise located on the substrate, and so positioned thereon that the distance from each other at a location adjacent the inner end, that is, adjacent the end facing the connecting end portion of the sensor, is greater than at the region of the substrate which is located within the tubular body.

The arrangement has the advantage that it can be easily made since conductive tracks need be applied only on a flat platelike element, which is simple and inexpensive, since all application steps can be carried out in a single plane. In accordance with a preferred embodiment of the invention, the substrate is trapezoidally shaped in the region facing the connecting end portion, the longer base line of the trapezoid being defined by the end of the plate-like substrate facing the connecting end portion.

DRAWINGS:

FIG. 1 is a longitudinal sectional view trough the sensor of the present invention, illustrated to an enlarged scale, the section being taken along line I—I of FIG. 2;

FIG. 2 is a cross-sectional view along line II—II of FIG. 1; and

FIG. 3 is a fractional longitudinal view along line III—III of FIG. 2, that is, rotated 90° with respect to FIG. 1.

DETAILED DESCRIPTION

The oxygen sensor 10—see FIGS. 1-3, has a metallic housing 11 which, at the outside thereof, is formed with a hexagonal nut 12, and includes a thread 13 to attach the sensor into a tapped opening of a pipe or tube carrying the gas to be analyzed or monitored. A ring-shaped sealing element 14 insures sealed seating of the housing 11 in the tube or pipe—not shown, the ring 14 being seated in a groove 15 between the nut 12 and thread 13 so that it cannot be removed or become lost. The sensor has a sensing end portion and a connecting end portion. The housing 11 has a groove 16 in the region facing the connecting end portion which is used to connect an extension sleeve 17 to the housing 11, for example by rolling-in a cylindrical tube into the groove 16. The sleeve 17 is radially inwardly extended to form a transverse wall 18, having a central opening 19, the sleeve 17 being deformed as seen at 20 to fit into the groove 16 of the housing 11.

The housing 11 has a longitudinal bore or opening 21 with a shoulder 22 which faces the sensing end portion of the sensor 10, and carries a ring-shaped sealing element 23. The sensing element 24, having a flanged end portion 25, engages a sealing element 23 interposed between a shoulder 22 and the flange 25 of the sensing element 24.

The sensing element 24 can be made in accordance with any one well known oxygen sensor construction, for example as described in German Utility Model DE-GbmS No. 81 01 584. Preferably, it is used to test the partial oxygen pressure in combustion exhaust gases, for example in the exhaust gases from internal combustion engines. The sensing element 24 has a solid electrolyte tube 26, closed off at the sensing end by a bottom cover 27. At the outside of the tube, that is, the side exposed to the test gas, a layer-like gas-pervious sensing electrode 28 is located; at the inside 29, a gas-pervious, layer-like counter or reference electrode 30 is located, exposed to a reference gas, for example ambient air. The sensing electrode 28 is connected to the housing 11 which, normally, is electrically grounded or connected to chassis of the vehicle with which it may be used. The measuring electrode 28 is secured to that housing via the sealing element 23, the sealing element being electrically conductive so that the sensing electrode is electrically connected to the grounded or chassis-connected housing 11. The counter or reference electrode 30 extends, preferably, to the inside of the bottom wall 27 and then to the end facing surface 31 remote from the measuring end portion, formed on the solid electrolyte tube 26. The lifetime of the structure can be increased by coating the sensing electrode 28 which, normally, is made of a very thin platinum layer, by a gas-pervious protective layer—not shown—and made, for example, of magnesium spinel.

Rather than using a solid electrolyte tube 26 with a closed bottom 27, it is also possible to use an open solid electrolyte tube which is open to the measuring gas at both the inside and the outside, in which case electrodes are preferably used which have, respectively, catalytic and non-catalytic effects.

The portion of the sensor element extending from the longitudinal bore 21 of the housing 11 towards the sensing end portion is protected by a protective tube 32, surrounding a projecting portion, formed with openings 33 for ingress and exit of measuring gases, and which is secured to the end portion of the housing 11 by a roll, interference or snap-in fit or the like. The protective tube 32 is provided to prevent abrasion by particles which are icluded within the measuring gas and to prevent rapid changes in temperature in the measuring or sensing gas from directly affecting the sensitive solid electrolyte tube and thereby damaging the tube.

A heating element 35 extends into the interior space 29 of the solid electrolyte tube 26. Preferably, the diameter of the solid electrolyte tube 26 decreases or tapers somewhat in the direction of the bottom 27.

In accordance with a feature of the invention, the heating element 35 is plate-like and includes an electrically insulating substrate plate 36 on which conductive tracks 37 are applied. The substrate 36 may be made, for example, of aluminum oxide and, in a preferred form, is so constructed that the terminal end portion thereof is wider than the portion which extends into the interior space 29 of the solid electrolyte tube 26. At least the end portion of the substrate 36, facing the terminal end, is essentially trapezoidal. The longer side of the trapezoid is formed by the end edge 36' of the plate 36.

The substrate 36 is approximately 0.8 mm thick. The conductive track 37 preferably is made of a platinum metal which may have ceramic additives; it can be applied to the substrate 36, preferably, by printing, although various other suitable application methods may be used. After printing, the tracks are sintered together with the substrate. Rather than using a platinum metal, other suitable materials can be used for the conductors 37, and rather than printing, other known processes of application may be used. The conductive track 37 is subdivided into:

(1) the heater element 37/1 applied to the portion of the substrate 36 close to the measuring end of the sensor; preferably, the heater element 37/1 is arranged in a meander track;

(2) two connecting track portions 37/2, which are wider than the individual track portions of the heater element 37/1 and extend up to the connecting end region of the substrate 36; and (3) the connecting end regions 37/3 which are located at the connecting end portion of the substrate 36 and are widened with respect to the connecting tracks 37/2. If necessary, and desirable, they may also be reinforced in thickness.

The reinforcement of the connecting regions 37/3 of the conductive track 37 can be effected by application of a suitable material which may be different from that of the track portions, for example by a layer of silver.

The track 37, excluding the connecting regions 37/3, can be coated by a thin protective coating (not shown for clarity of the drawing), for example made of magnesium spinel.

The widening of the substrate 36 permits formation of connecting regions 37/3 of suitable size and such spacing from each other that sufficient space is available to provide for contacting engagement of connecting conductors.

The facing surface 31 of the sensing element 24, remote from the measuring end, on which the layer-like counter electrode 30 terminates, has a ring-shaped connection element 38 applied thereto which surrounds the plate-like heater 35. The connecting element 38 has a sleeve-like shaft 39 (FIG. 1) which likewise surrounds heater element 35 and which extends in the direction towards the connecting end portions of the sensor.

The space between the sensor element 24, the housing 11, and a stopper 69 retains two insulating sleeves 40, 41 which are preferably made of a ceramic material, such as aluminum oxide, and which are held by a guide sleeve 42 coaxially, within the oxygen sensor 10. The guide sleeve 42, at the measuring end portion, is secured in the longitudinal bore 21 of the housing 11, for example by a press fit or other deformation, and has an externally directed flange 43 at the end remote from the measuring end which extends close to the closing sleeve 17. The ring space 44 between the closing sleeve 17 and the guide sleeve 42 forms a barrier with respect to dampness which might enter the sensor together with the air forming the reference gas in the region between the measuring gas end portion of the connecting sleeve 17 and the housing 11. A spring, such as cup spring 45, is located between the flange 43 of the guide sleeve 42 and the bottom 18 of the sleeve 17, the cup spring being supported on the one hand on the bottom 18 of the sleeve 17 and, on the other, with mechanical bias, on a coaxial seat 46 of the insulating sleeve 40. Due to the mechanical tension of the element 45, the first insulating sleeve 40 engages with its end surface 47 on the portion of the ring 48, which is remote from the measuring end portion, of the second insulating sleeve 41 and thus against the end surface 49 of the second sleeve 41 and on the contact element 38 which is electrically connected to the counter electrode 30.

The second insulating sleeve 41 has a longitudinal slit 50 which surrounds the plate-like heater 35. The end portion of the slit 50 engages the shaft 29 of the contacting element 38. A longitudinal bore 51, parallel to the axis of the sensor and to the longitudinal slit 50 of the second insulating tube 41 carries a connecting conductor 52 which at the measuring end portion is secured by any suitable process, for example by welding, to the shaft 39 of the contacting element 38. The connecting end portion of the conductor 52 is carried through a bore 53 in the first insulating sleeve 40 and extends outwardly therefrom.

A recess 54 is formed at the end surface 47 facing the measuring end portion, of the first insulating sleeve 40 which, in axial direction, has a flat engagement surface 55 for the terminal end portion of the heating element 35 and which has a shoulder 55', facing the measuring end portion. The end portion of the heater 35 engages the engagement surface 55. The end edge 36' of the substrate 36 engages the shoulder 55' of the recess 54 in the insulating sleeve 40. Two additional guide slits 56, 57 are formed in the recess 54, extending longitudinally within the insulating sleeve 40 and shaped to receive and locate in position a springy connecting element, forming a compression terminal 58, 59, respectively. The springy connecting elements 58, 59, preferably, are made of metallic wire which is bent backwardly upon itself in loop or hook form at the side facing the measuring end portion. The first insulating sleeve is formed with through-holes 60 for the respective connection elements 58, 59—see FIG. 1—which terminate in the corresponding guide slits 56, 57. The end portions of the connecting elements 58, 59 extend from the insulating sleeve 40 at the terminal end side thereof. The portions of the connecting elements 58, 59, at the region where they leave the through-holes 60 and enter the respective guide slits 56, 57, are laterally offset to form a stepped shoulder extending outwardly, and the outwardly angled offset portion 62 engages the respective shoulder 61 formed in the insulating sleeve 40. The stepped offset portion 62 of the connecting elements 58, 59 is used to securely hold the respective connecting elements 58, 59 in position, and insure against dislocation or removal from their predetermined positions, for example under tension, twist or vibration, which might be transmitted to the connecting elements by wire ends forming part of a connecting cable 63. The connecting cable 63 has connecting wires 64/1 and 64/2. The end portions of the connecting wires 64/1 and 64/2 are connected with the terminals of the connecting elements 58, 59 projecting towards the connecting end from the insulating sleeve 40, by connecting sleeves 65 which are suitably joined to the respective connecting wires 64/1, 64/2, for example by deformation, welding, soldering or the like.

A connecting sleeve 65 also connects the end portion of the current conductor 52 projecting from the insulating sleeve 40 with the connecting wire 64/3 of the cable 63. The connecting wire 64/3 is used to transmit the measured sensed values or voltage parameters which occur between ground or chassis connection defined by the outer electrode and the inner electrode connected to the connecting cable 64/3.

The offset angled portion 62 of the connecting elements 58, 59 extends, at the measuring side, to an abutment surface 66 formed by the end face of the second insulating sleeve 41. The springy connection elements 58, 59 engage the end surface 66 of the second insulating sleeve 41 and then are bent over themselves towards the offset portion 62. The free end portions of the connecting elements 58, 59 are bent inwardly, as seen at 67, to form a connecting projection or connecting bump engaging the respective connection region 37/3 on the heater 35 to provide mechanical bias thereagainst. The region of the bend 67 can be slightly flattened at the outside of the bump or tip formed thereby, so that the pressure between the respective connecting region 37/3 and the respective connecting element 58, 59 will not lead to damage of the connection region 37/3.

Different forms of connection may be used, for example instead of the offset angled portion 62, the connecting elements 58, 59 may be shaped in wavy or undulating form in order to reliably insure that the connecting elements will be resistant against tension and vibration which may be transmitted by the connecting wires 64/1, 64/2 of the cable 63 to the connecting elements 58, 59.

In accordance with a preferred embodiment, an insulating stopper 69 is provided, which surrounds the connecting sleeves 65, and is seated at the end of the first insulating sleeve 40. Preferably, the stopper is made of elastic insulating material, such as rubber or plstic, tightly and sealingly surrounding the connecting sleeve 65 and the portions of the connecting wires 64/1, 64/2, 64/3. The stopper 69 is formed with a flange 71, facing the measuring end portion, and is fitted, sealingly, against the surface 72 at the outside of the bottom 18 of the sleeve 17, while surrounding the end portion of the ceramic insulating sleeve 40—see FIG. 1. The surface 73 of the insulating stopper 62 is jacketed by a metallic end sleeve 74 which is expanded at the side facing the measuring end portion of the sensor 10 and extends over the end portion of the sleeve 17. It is secured to the sleeve 17 by any suitable means, for example by spot-welding, press-fitting, or other connection, as desired; the metallic sleeve 74 holds the insulating resilient stopper 69 under mechanical compression.

The heating element 35 with its layer-like heating element and the associated connecting tracks and connecting regions can be located on one or both major planes of the plate-like substrate 36. If so used, it is of advantage to connect the heating elements 37/1 (FIG. 3) of the heating element 35.

The arrangement of the heater 35, in plate form, and positioned and shaped as described, is a particularly desirable structure suitable for mass production, since it can be made inexpensively. The sensor of this type is particularly suitable to determine the oxygen content in gases resulting from a combustion process, such as exhaust gases from an internal combustion engine, exhaust gases in flues, burners, furnaces, and the like.

We claim:

1. Internally heated oxygen sensor, particularly to determine the oxygen content in exhaust gases from a combustion process, especially from an internal combustion engine, having
   a tubular oxygen-ion-conductive body (26);
   a first electrode (28) secured to an outer surface of the tubular body;
   a housing (11) retaining said tubular body in a predetermined position, projecting from the housing;
   a heater element (35) located within the tubular body and having an inner end projecting from the tubular body inside the housing, and an outer end located in the vicinity of the projecting end of the tubular body; and
   means for retaining the heater element in position in the housing, and within the tubular body,
   wherein, in accordance with the invention,
   the heater element (35) comprises
   a plate-like substrate (36) of insulating material having a dimension at the inner end which is wider than the dimension of the projecting end; and
   two electrical connection tracks (37/2) located on the plate-like substrate, and being positioned thereon to have a greater distance from each other at a location adjacent the inner end than in the region of the plate-like substrate which is located within the tubular body (26), the connection tracks leading to electrical heating conductors (37/1), said connection tracks and said heating conductors being formed as surface conductive tracks on the substrate (36).

2. Sensor according to claim 1, wherein the substrate, at the location adjacent the inner end, is essentially trapezoidal, having a longer base line forming the edge (36') of the substrate (36) at the inner end.

3. Sensor according to claim 1, wherein the sensor (10) includes means (40) forming an abutment surface (55), extending essentially longitudinally within the sensor;

the plate-like substrate (36) engages the abutment surface (55) with one flat surface of the plate-like substrate;

and further including resiliently biassed compression spring elements (58, 59) engaging the substrate in the region of the inner end and pressing the substrate against the abutment surface (55).

4. Sensor according to claim 3, wherein the compression spring elements are metallic and comprise connection means leading to external connections (64/1, 64/2);

the heating conductor elements include terminal portions (37/3), and the compression spring elements engage the terminal portions, and are located at the level of the terminal portions as well as the level of the abutment surface.

5. Sensor according to claim 4, wherein the compression elements comprise bent-over spring wires; the means (40) forming an abutment surface include an insulating body formed with two parallel chambers therein, each chamber receiving a respective bent-over wire and engaging a respective terminal portion (37/3) of the electrical connection tracks.

6. Sensor according to claim 5, wherein the chambers are elongated slots, and the insulating body comprises a ceramic element, receiving the bent-over spring wires, the bent-over spring wires being bent into hook shape bearing, with one side of the hook, against an inner wall of a respective slot and, with the other side of the hook, against a terminal portion (37/3) of the connection tracks on the plate-like substrate (36), thereby pressing the plate-like substrate against the abutment surface (55).

7. Sensor according to claim 1, wherein said tubular body (26) and said plate-like substrate (36) are correspondingly tapered.

* * * * *